United States Patent [19]
Saito et al.

[11] Patent Number: 5,618,562
[45] Date of Patent: Apr. 8, 1997

[54] SPHERICAL GRANULE, PRODUCTION METHOD THEREOF AND MEDICINAL PREPARATION USING SAID GRANULE

[75] Inventors: Hiroshi Saito; Toshio Mikami; Nagayoshi Myo, all of Tokyo, Japan

[73] Assignee: Freund Industrial Co., Ltd., Tokyo, Japan

[21] Appl. No.: 544,061

[22] Filed: Oct. 17, 1995

Related U.S. Application Data

[63] Continuation of Ser. No. 176,969, Jan. 3, 1994, abandoned.

[30] Foreign Application Priority Data

Jan. 12, 1993 [JP] Japan .................... 5-003218

[51] Int. Cl.$^6$ .................... A61K 9/14
[52] U.S. Cl. .................. 424/489; 424/488; 424/490
[58] Field of Search ................... 424/489, 488, 424/490

[56] References Cited

U.S. PATENT DOCUMENTS

| | | | |
|---|---|---|---|
| 4,946,359 | 8/1990 | Christen | 425/222 |
| 5,189,148 | 2/1993 | Akiyama | 530/399 |
| 5,260,072 | 11/1993 | Roche | 424/490 |
| 5,283,065 | 2/1994 | Doyon | 424/467 |

FOREIGN PATENT DOCUMENTS 4-283520  12/1993  Japan.

OTHER PUBLICATIONS

"Summary of the lectures presented at the 7th Symposium on Preparation and Particle Design", Oct. 24 and 25, 1990, p. 89.
Miyake et al. "Spheronizing Mechanism and Properties of Spherical Granules", Yakuzaigaku (Pharmacology) vol. 33, No. 4 (1973) pp. 161–165.

*Primary Examiner*—Thurman K. Page
*Assistant Examiner*—William E. Benston, Jr.
*Attorney, Agent, or Firm*—Kane, Dalsimer, Sullivan, Kurucz, Levy, Eisele and Richard, LLP

[57] ABSTRACT

The spherical granules useful as a precipient for medicines and foods, and a production method thereof. A spherical granule comprises 95% by weight or more of lactose, and has a long diameter/short diameter ratio of 1.2 or less, and, when aggregated, a bulk density of 0.7 g/ml or more and an angle of repose of 35° or less. The spherical granule is produced by feeding lactose particles into a granulating and coating apparatus equipped with a horizontal rotary disk having a smooth surface to contact with the granules, and by spraying lactose solution while the above-mentioned rotary disk is rotated.

7 Claims, 2 Drawing Sheets

× - Coated particle of Example 5
△ - Double-coated particle of Example 6 (coating amount: 3 % by weight)
○ - Double-coated particle of Example 6 (coating amount: 4 % by weight)

- Ascorbic acid matrix layer
- Spherical granule (nucleus)
- Film layer (All dimensions are inside dimensions, and expressed in millimeter)

SPHERICAL GRANULE, PRODUCTION METHOD THEREOF AND MEDICINAL PREPARATION USING SAID GRANULE

This application is a continuation of application Ser. No. 08/176,969, filed Jan. 3, 1994, now abandoned.

BACKGROUND OF THE INVENTION

1. Field of the Invention

This invention relates to spherical granules and the production method thereof and, in particular, to spherical granules comprising lactose, which are useful excipients for medicines and foods.

2. Related Art Statement

Recentlly, controlled release techniques for medicines (e.g. sustained release drugs and enteric coating drugs) have made remarkable progress. Among them, there is widely used a release control method, wherein the surface of uniform-size spherical particles is coated with a medicinal layer and a release control layer, and, if necessary, several kinds of coated particles having different thickness of a coating layer from one another are put into a capsule to obtain a preparation having more uniform sustained release.

Usually, the spherical particles used in this method are made of sucrose or a mixture of sucrose and starch. To obtain the spherical particles, the nuclei of the crystalline sucrose are fed into a centrifugal fluidized granulating apparatus, and, then, fine powder of sucrose or a mixture of sucrose and starch is sprayed into the granulating apparatus to be coated on the nuclei while sucrose solution or a mixed solution of sucrose and starch is sprayed as a binder.

However, the conventional spherical particles made of sucrose or sucrose and starch mixture and the conventional production method have the following deficiencies.

(1) The water-solubility of sucrose Is very high, and, therefore, use of an aqueous liquid to coat the surface of the spherical particles with medicinal and release control layers may cause the particles to agglomerate with one another and stick to the wall of the granulating apparatus. Furthermore, at the time of application of the medicinal preparation made with this nuclei, sucrose may come out of the preparation as water infiltrates, thereby the preparation losing its shape and sustained-release property before attaining its object.

(2) The calorific value of sucrose may be disadvantageous to diabetics.

In order to eliminate these deficiencies, the use of spherical particles made singly of crystalline cellulose was suggested for release control purposes (Summary of the lectures presented at the 7th Symposium on Preparation and Particle Design; Oct. 24 and 25, 1990, p.89).

Although spherical particles made of crystalline cellulose have eliminated the above-mentioned deficiencies of the spherical particles made of sucrose or a mixture of sucrose and starch, they pose new and difficult problems of their own. Since crystalline cellulose Is insoluble in water, it takes a long time to break down, and sometimes the release-control layer prevents complete release of the medicine or the spherical particles are excreted without being digested arousing patients' suspicion on the effectiveness of the preparation.

Another improved method using lactose granules has also been proposed, and a preparing method and physical properties of such spherical granules have been disclosed in Miyake et al. "Spheronizing Mechanism and Properties of Spherical Granules", *YAKUZAIGAKU* (Pharmacology) Vol.33, No.4 (1973) pp.161–165.

However, the lactose granules obtained by the method described in the above article were far from spherical, the aspect ratio (long diameter/short diameter ratio) of the granules being 1.3 or more, and, as aggregate, the bulk density was 0.6 g/ml or less, and, therefore, It lacks free flowing property and it is difficult to fill up a capsule with correct quantity.

The purpose of the present invention is to provide new spherical granules that are free of the above-mentioned deficiencies of the spherical particles made of sucrose or a mixture of sucrose and starch, crystalline cellulose or lactose, and to provide a production method thereof.

SUMMARY OF THE INVENTION

The spherical granule according to the present invention comprises 95% by weight or more of lactose, and has a long diameter/short diameter ratio of 1.2 or less, an aggregate bulk density of 0.7 g/ml or more and an angle of repose of 35° or less. The above lactose content (95% by weight or more) is given in terms of non-volatile contents.

According to the present invention, other than lactose, components contained in the spherical granule are not restricted. For instance, saccharides such as starch, dextrin, pullulan, and sucrose; cellulose; and binders such as hydroxypropyl cellulose, methylcellulose, hydroxypropyl methylcellulose, and carboxymethylcellulose can all be used. However, permissible components are not limited to these materials, and other materials can be used as well. Further, the granule made substantially only of lactose is also preferable.

According to the present invention, the long diameter/short diameter ratio of the spherical granule is 1.2 or less. When the surface of the granule is coated with a medicinal layer and a release control layer, it is essential for proper release control that these layers are of even thickness. The closer the granule is to a perfect sphere, the more even the thickness of each coating layer becomes. In order to macroscopically determine the degree of sphericity of the granules, it is advisable to measure the long diameter/short diameter ratio. Granules with a ratio exceeding 1.2 are inappropriate as nuclei to be used for release control purpose.

Of the properties of granules as aggregate, both bulk density and angle of repose are important. Bulk density varies with granule shape, density, and particle size distribution. In the case of granules used for release control purposes, a sharp distribution of particle sizes is prerequisite; bulk density serves as a composite indicator of shape and density.

In the case of the granules having the long diameter/short diameter ratio of 1.2 or less, semimicroscopic particle formations such as surface unevenness and angular protrusions affect bulk density. The larger such semimicroscopic deviations from the perfect sphere are, the smaller the bulk density becomes. Granules with lower density are lower in hardness.

Accordingly, a larger bulk density is preferable. The inventors have found that the bulk density of lactose granules needs to be 0.7 g/ml or more, and preferably 0.75 g/ml or more for practical applications.

Meanwhile, the angle of repose is also related to the above-mentioned semimicroscopic shape of the granules and their surface roughness. The inventors have found that for granules to provide good release control, the angle of repose should be 35° or less, and preferably, 33° or less.

In order to produce spherical granules with these characteristics, it is suitable to use a granulating and coating apparatus equipped with a horizontal rotary disk, wherein the disk surface is smooth at its portion contacting with granules. Several granulating and coating apparatuses that meet this requirement are available, including centrifugal fluidized granulating apparatuses ("CF Granulator" manufactured by Freund Industrial Co., Ltd.) and granulating and coating apparatuses equipped with a smooth-faced rotary disk having a ventilating portion in the bottom of the fluidized bed ("Spir-A-Flow" and "Flow Coater with Rotor Container", both manufactured by Freund Industrial Co., Ltd.).

According to a study by the inventors, the granulating apparatus used in the above-mentioned Miyake et al. article on the lactose granules (*YAKUZAIGAKU* (Pharmacology) Vol.33, No.4 (1973) pp.161–165) (MARUMERIZER, manufactured by Fuji Powdal Co.) did not have a smooth rotary disk; instead, it had a friction plate. This difference is one of causes of the failure to produce good lactose granules.

In the production method according to the present invention, lactose particles are fed to the above-mentioned granulating and coating apparatus. These particles do not need to have been granulated preliminarily. Crystalline lactose, powder lactose, mixtures of them, or mixtures containing other components may be used as "lactose particles".

The lactose particles are then granulated by rotating the rotary disk of the apparatus, while spraying lactose solution into the granulating and coating apparatus. The lactose solution used here can be a system in which lactose is not dissolved completely in water. A system in which fine particles of lactose are dispersed can be used also. When an unsaturated solution of lactose is used, its lactose concentration is preferably about 10–58% by weight. When solution with a lactose concentration exceeding 30% by weight is used, it is necessary to keep the solution heated in order to prevent the deposition of coarse particles of lactose.

If necessary, other saccharides, binders, surfactants or medicinal components can be added to this lactose solution. Also, as a solvent for lactose, other than water alone, a mixture of water and other solvents such as ethyl alcohol can be used.

This method of production allows high yield of production of the spherical lactose granules with the above-mentioned suitable characteristics for release control.

The spherical granules according to the present invention can be used for obtaining sustained-release medicinal preparations and enteric-coated medicinal preparations by coating them with a medicinal layer and a release control layer successively, or by coating them with a mixed layer of a medicine and a release control agent.

According to another aspect of the present invention, the spherical granule may by itself contain 5% by weight or less of a medicinal component. This granule can be used as a preparation by itself or by coating a release control layer such as a sustained-release layer or an enteric coating layer on its surface.

Since the present invention can provide granules of uniform grain size, it can produce preparations in which distribution of dissolution rates due to different grain sizes is minimized and the distribution of the content of the medicine is very sharp. Further, the spherical granules according to the present invention can be utilized as excipients not only for medicines but also for foods.

BRIEF DESCRIPTION OF THE DRAWINGS

Hereunder, the present invention will be further described by way of examples in conjunction with the accompanying drawings in which.

DETAILED DESCRIPTION OF THE PREFERRED EMBODIMENT

In the following Examples, the long diameter/short diameter ratio of the granule was obtained by measuring long and short diameters of 50 granules from microscopic photographs and taking their mean value. The bulk density was measured in accordance with the Japanese Industrial Standard (JIS K-6721).

Figure 3:
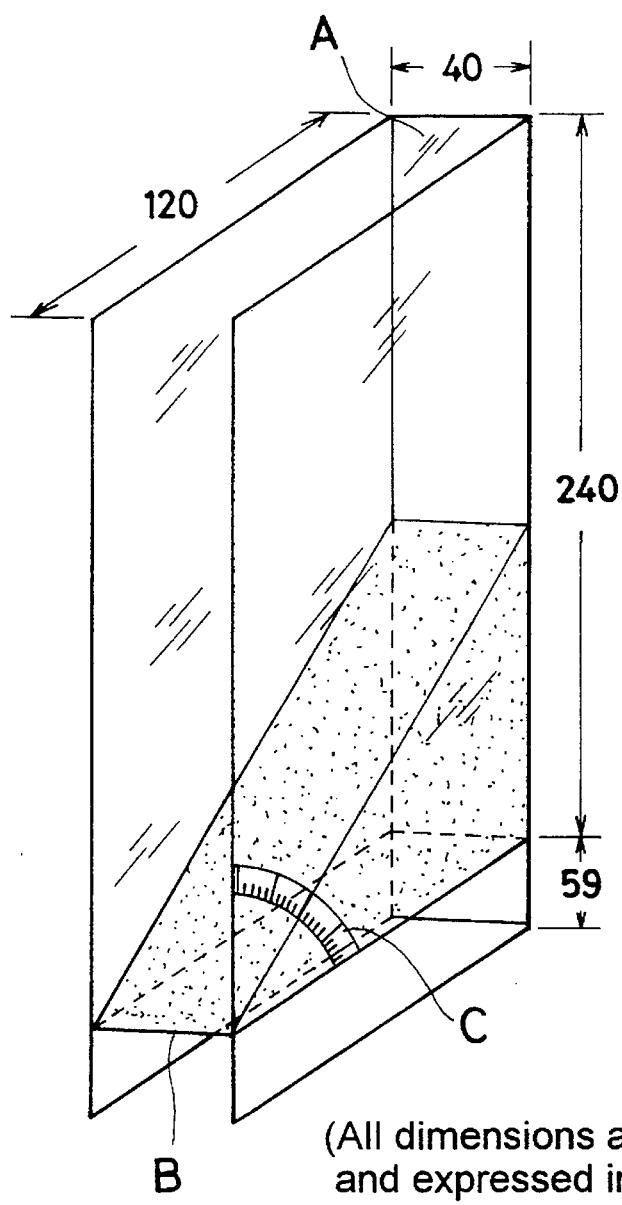
FIG. 3 is a diagram explaining the measuring method used to determine the angle of repose.

The angle of repose was measured in accordance with the Nogami-Sugihara method illustrated in FIG. 3. Specifically, the tool shown in FIG. 3 is made by pasting glass plates. The horizontal plane B is a glass bed, and a protractor C is mounted to measure an angle to the plane B. About 200 ml of a sample was slowly poured into the tool through a funnel along the vertical wall A until the sample flowed out of the opening of the tool. The angle formed by the sample surface and the horizontal plane (Plane B) was then read using the protractor C to determine the angle of repose.

[EXAMPLE 1]

Two-hundred-fifty grams of crystalline lactose with a mean grain size of about 200 μm was fed into a centrifugal fluidized granulating apparatus ("CF-360" manufactured by Freund Industrial Co., Ltd.), and rotated at 220 rpm. Then, 600 g of lactose powder with a mean grain size of about 40 μm was sprayed while 1 kg of 40% by weight lactose solution was sprayed for 1 hour.

By this method, spherical granules of 420–300 μm were obtained at a yield of 82.4%. The long diameter/short diameter ratio of these spherical granules was 1.11, and the bulk density and the angle of repose were 0.79 g/ml and 31.7°, respectively.

[EXAMPLE 2]

One-hundred-fifty grams of crystalline lactose with a mean grain size of about 240 μm and 750 g of lactose powder with a mean grain size of about 40 μm were fed into a fluidized bed granulating and coating apparatus equipped with a rotary disk which has a ventilation net ("SFC-5" manufactured by Freund Industrial Co., Ltd.). Air at 80° C. was supplied through the disk at a rate of 1 m³/minute and through a slit between the disk and the side wall at 1 m³/minute, and, while the rotary disk was rotated at 300 rpm, 2 kg of 25 by weight lactose solution was sprayed for 50 minutes to obtain granules.

By this method, spherical granules of 710–500 μm were obtained at a yield of 78.9 %. The long diameter/short diameter ratio of these spherical granules was 1.14. Bulk density and angle of repose were 0.72 g/ml and 32.3° respectively.

[EXAMPLE 3]

Five hundred grams of lactose powder with a mean grain size of about 40 µm, 50 g of pullulan and 500 g of water were mixed by a kneader, and preliminarily granulated by a cylindrical squeezing granulator with a 0.3 mm mesh screen. Seven hundred grams of the pre-granulated particles were fed into a centrifugal fluidized granulating apparatus ("CF-360"), and 350 g of lactose powder with a mean grain size of about 40 µm was sprayed while spraying 700 g of 50% by weight lactose solution for 40 minutes, in final granulation.

By this method, spherical granules of 590–420 µm were obtained at a yield of 86.5%. The lactose content of the spherical granules was 96.6%, the long diameter/short diameter ratio was 1.07, bulk density was 0.77 g/ml and the angle of repose was 31.8°.

[EXAMPLE 4]

The same granulation method as in Example 1 was employed except for the addition of 0.5% by weight of reserpine with a mean grain size of about 15 µm, the percent being taken based on the amount of the crystalline lactose. By this method, spherical granules of 420–300 µm were obtained at a yield of 82.0%. The reserpine content in the spherical grains was 0.1% by weight, the long diameter/short diameter ratio was 1.11, bulk density was 0.79 g/ml and the angle of repose was 31.6°.

The uniformity of reserpine content of these spherical granules was examined and found to range from 0.097 to 0.104% by weight. For comparison, the reserpine content was examined on samples obtained by adding 0.1% by weight reserpine to powdered lactose with a mean grain size of about 40 µm, and rotating and mixing them for 30 minutes in a V-type mixer. Samples were taken from several points in the mixer, and the reserpine content proved to be 0.090–0.121% by weight.

[EXAMPLE 5]

Five hundred grams of the spherical granules obtained in Example 2 were fed into a centrifugal fluidized granulating apparatus ("CF-360"). Using these granules as nuclei, a powder mixture of 100 g of ascorbic acid in accordance with the Japanese Pharmacopoeia, 300 g of lactose and 100 g of corn starch was sprayed into the granulating apparatus. At the same time, a mixture of 20% by weight ethanol solution of ethyl cellulose and shellac (weight ratio 1:1) was sprayed as a binder, to obtain coated particles.

Figure 1:
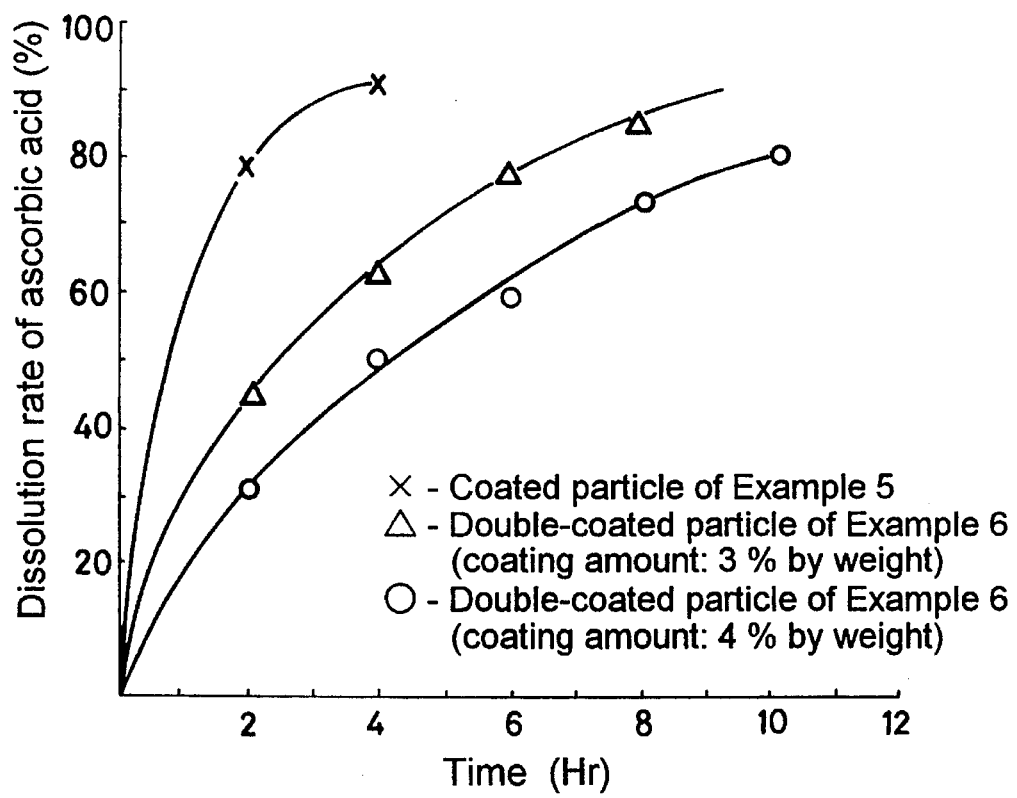
FIG. 1 is a graph showing dissolution rates of ascorbic acid in examples of medicinal preparations according to the present invention.

FIG. 1 presents ascorbic acid dissolution rates of the coated particles obtained. As shown in the figure, these coated particles by themselves demonstrated the sustained-release property because of the matrix of ethyl cellulose and shellac, but dissolution rate was slightly higher. The dissolution test was performed using the paddle method with 100 rotations employing an automatic dissolution testor ("DT-600" manufactured by Nihon Bunkou Kogyo K.K.) according to the Japanese Pharmacopoeia.

[EXAMPLE 6]

Figure 2:
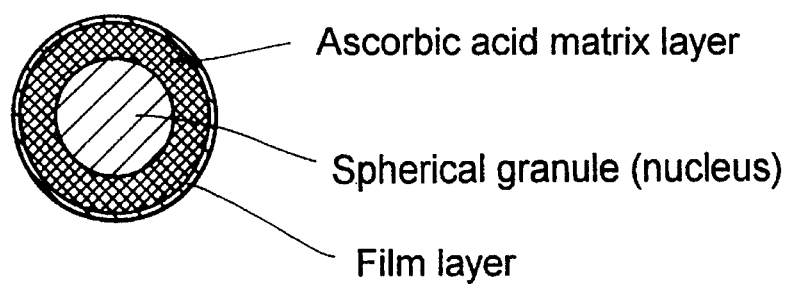
FIG. 2 is a cross-sectional view showing an example of medicinal preparation according to the present invention.

Onto the coated particles obtained in Example 5, was sprayed a mixture of 2.5% by weight ethanol solution of an ethyl cellulose and shellac (weight ratio 1:1) using a centrifugal fluidized granulating apparatus ("CF-360") to obtain double-coated particles. FIG. 2 illustrates the cross-section structure of the thus-obtained double-coated particle. FIG. 1 gives the ascorbic acid dissolution rates of two kinds of double-coated particles with coating amounts of 3 and 4% by weight respectively.

[EXAMPLE 7]

Crystalline lactose with a mean grain size of about 220 µm was fed into a centrifugal fluidized granulating apparatus ("CF-360"), and was rotated at 220 rpm. Then, 850 g of powdered lactose with a mean grain size of about 40 µm was sprayed while 250 g of 2% by weight hydroxypropyl cellulose solution were sprayed for 20 minutes.

By this method, spherical granules of 500–355 µm in size were obtained at a yield of 78.2%. The long diameter/short diameter ratio of these spherical granules was 1.13, and the bulk density and the angle of repose were 0.80 g/ml and 31.4°, respectively.

The spherical granules according to the present invention were made mainly of lactose, and, therefore, they dissolve more slowly than conventional spherical granules made of sucrose or a mixture of sucrose and starch and retain their shape well, and have the merit of low calorific value. The obtained granules are also free of such deficiency of the spherical granules made mainly of slightly water-soluble crystalline cellulose that breakdown never happens, thus making them ideal as the nuclei of release-control medicinal preparations.

What is claimed is:

1. A spherical granule comprising at least 95% by weight of lactose, which has a long diameter/short diameter ratio of 1.2 or less, and, when aggregated, has a bulk density of 0.7 g/ml or more, and an angle of repose of 35 or less, wherein said granule is produced by a method comprised of feeding particles comprising lactose to a granulating and coating apparatus equipped with a rotary disk having a smooth-faced portion for contacting with the granules; and spraying a lactose solution and optionally a binder while the rotary disk is rotated.

2. The spherical granule according to claim 1, further comprising less than 5% by weight of medicine.

3. The spherical granule according to claim 1, further comprising a binder.

4. The spherical granule according to claim 1, which, when aggregated, has a bulk density of 0.75 g/ml or more and as angle of repose of 33° or less.

5. A medicinal preparation obtained by coating a surface of the spherical granule according to claim 1 with at least one layer selected from the group consisting of a medicinal layer and a release control layer.

6. The medicinal preparation according to claim 5, characterized in that the medicinal preparation is a sustained-release medicinal preparation.

7. The medicinal preparation according to claim 5, characterized in that the medicinal preparation is an enteric-coated medicinal preparation.

* * * * *